(12) United States Patent
Croizat et al.

(10) Patent No.: US 9,220,821 B2
(45) Date of Patent: Dec. 29, 2015

(54) FASTENER FOR A NEGATIVE PRESSURE THERAPY DEVICE

(71) Applicant: Paul Hartmann AG, Heidenheim (DE)

(72) Inventors: Pierre Croizat, Herbrectingen (DE); Axel Eckstein, Heidenheim (DE); Jurgen Hofstetter, Heidenheim (DE); Andreas Mahler, Blaubeuren-Asch (DE); Andreas Weinberg, Stuttgart (DE); Martin Ruf, Tubingen (DE); Astrid Fonfara-Dorr, Ulm (DE)

(73) Assignee: Paul Hartmann AG, Heidenheim (DE)

( * ) Notice: Subject to any disclaimer, the term of this patent is extended or adjusted under 35 U.S.C. 154(b) by 172 days.

(21) Appl. No.: 13/866,443

(22) Filed: Apr. 19, 2013

(65) Prior Publication Data

US 2013/0289536 A1    Oct. 31, 2013

Related U.S. Application Data

(60) Provisional application No. 61/640,874, filed on May 1, 2012.

(30) Foreign Application Priority Data

Apr. 26, 2012  (DE) .................. 10 2012 008 301

(51) Int. Cl.
| | |
|---|---|
| *A61M 1/00* | (2006.01) |
| *F16M 11/04* | (2006.01) |
| *A61M 5/14* | (2006.01) |
| *F16B 2/06* | (2006.01) |

(Continued)

(52) U.S. Cl.
CPC ............ *A61M 1/0023* (2013.01); *A61M 1/0088* (2013.01); *A61M 5/1415* (2013.01); *F16B 2/06* (2013.01); *F16B 2/065* (2013.01); *F16B 2/22* (2013.01); *F16M 11/041* (2013.01); *F16M 13/02* (2013.01); *F16M 13/022* (2013.01); *A61B 2560/045* (2013.01); *A61B 2560/0431* (2013.01); *A61B 2560/0443* (2013.01); *A61G 7/0503* (2013.01); *A61M 2209/082* (2013.01); *A61M 2209/084* (2013.01); *A61M 2209/086* (2013.01); *A61M 2209/088* (2013.01)

(58) Field of Classification Search
CPC . A61G 7/0503; A61G 3/001; A61G 2210/00; A61G 2210/20; A61G 2210/30; A61M 2209/088; A61M 5/1414; A61M 5/1415; A61M 5/1417; A61M 1/00; A61M 1/0001; A61M 1/0003; A61M 1/0023; A61M 1/0058; A61M 1/0066; A61M 1/008; A61M 1/0086; A61M 1/0088; A61M 1/009; A61M 2205/8206; A61M 2205/82; A61M 2209/086; A61M 2209/082; F16B 2/06; F16B 2/065; F16B 2/22; F16M 13/02; F16M 13/022; F16M 2200/00; F16M 2200/02; F16M 2200/021; F16M 2200/022; F16M 2200/024; F16M 2200/025; F16M 2200/027; F16M 2200/028; F16M 11/041; A61B 2560/045; A61B 2560/0443; A61B 2560/0431

See application file for complete search history.

(56) References Cited

U.S. PATENT DOCUMENTS

| | | | | |
|---|---|---|---|---|
| 4,844,397 A | * | 7/1989 | Skakoon et al. | ......... 248/231.71 |
| 5,472,317 A | * | 12/1995 | Field et al. | .................... 417/234 |

(Continued)

*Primary Examiner* — Adam Marcetich
(74) *Attorney, Agent, or Firm* — Dilworth & Barrese LLP (57) ABSTRACT

The invention relates to a fastening device for a negative-pressure therapy appliance, in particular for negative-pressure treatment of wounds on the human or animal body, comprising a holding means, a hollow body and a receiving area.

18 Claims, 4 Drawing Sheets

(51) Int. Cl.
  *F16B 2/22* (2006.01)
  *F16M 13/02* (2006.01)
  *A61G 7/05* (2006.01)

(56) References Cited

U.S. PATENT DOCUMENTS

| | | | | |
|---|---|---|---|---|
| 5,580,151 | A * | 12/1996 | Chen | 362/549 |
| 5,782,611 | A * | 7/1998 | Neftel et al. | 417/234 |
| 5,845,885 | A * | 12/1998 | Carnevali | 248/181.1 |
| 6,183,417 | B1 * | 2/2001 | Geheb | G06F 19/3406 600/301 |
| 6,315,182 | B1 * | 11/2001 | Chen | 224/420 |
| 6,409,131 | B1 * | 6/2002 | Bentley et al. | 248/219.4 |
| 6,450,436 | B1 * | 9/2002 | Tsuji et al. | 242/400.1 |
| 6,637,707 | B1 * | 10/2003 | Gates et al. | 248/224.7 |
| 7,017,243 | B2 * | 3/2006 | Carnevali | 24/523 |
| RE43,806 | E * | 11/2012 | Carnevali | 248/181.1 |
| 2005/0269473 | A1 * | 12/2005 | Carnevali et al. | 248/311.2 |
| 2006/0231713 | A1 * | 10/2006 | Crain et al. | 248/309.1 |
| 2006/0284040 | A1 * | 12/2006 | Nixon et al. | 248/311.2 |
| 2007/0022582 | A1 * | 2/2007 | Carnevali | 24/523 |
| 2007/0204727 | A1 * | 9/2007 | Lee et al. | 81/177.9 |
| 2007/0299358 | A1 * | 12/2007 | Bertinetti et al. | 600/529 |
| 2008/0023615 | A1 * | 1/2008 | Scarcello | 248/480 |
| 2008/0077078 | A1 * | 3/2008 | Locke et al. | 604/35 |
| 2008/0272254 | A1 * | 11/2008 | Harr et al. | 248/218.4 |
| 2008/0281168 | A1 * | 11/2008 | Gibson | A61B 5/0205 600/301 |
| 2008/0296454 | A1 * | 12/2008 | Carnevali | 248/231.71 |
| 2008/0302946 | A1 * | 12/2008 | Bury | 248/634 |
| 2009/0005747 | A1 * | 1/2009 | Michaels et al. | 604/319 |
| 2009/0140113 | A1 * | 6/2009 | Carnevali | 248/223.41 |
| 2009/0168308 | A1 * | 7/2009 | O'Brien et al. | 361/679.01 |
| 2009/0281454 | A1 * | 11/2009 | Baker et al. | 600/573 |
| 2010/0185164 | A1 * | 7/2010 | Hartwell et al. | 604/313 |
| 2010/0191199 | A1 * | 7/2010 | Evans et al. | 604/319 |
| 2010/0261979 | A1 * | 10/2010 | Kiani | A61B 5/0002 600/301 |
| 2011/0040288 | A1 * | 2/2011 | Eckstein et al. | 604/543 |
| 2011/0066110 | A1 * | 3/2011 | Fathallah et al. | 604/151 |
| 2011/0108689 | A1 * | 5/2011 | Dorris et al. | 248/221.12 |
| 2011/0168857 | A1 * | 7/2011 | Svedman et al. | 248/218.4 |
| 2011/0223802 | A1 * | 9/2011 | Zeller et al. | 439/529 |
| 2012/0086437 | A1 * | 4/2012 | Lin | 324/156 |
| 2012/0184932 | A1 * | 7/2012 | Giezendanner et al. | 604/319 |
| 2012/0209228 | A1 * | 8/2012 | Croizat et al. | 604/319 |

* cited by examiner

FASTENER FOR A NEGATIVE PRESSURE THERAPY DEVICE

CROSS REFERENCE TO RELATED APPLICATIONS

The present application claims priority to U.S. provisional application No. 61/640,874 filed May 1, 2012, which is herein incorporated by reference.

BACKGROUND

The invention relates to a fastening device for a negative-pressure therapy appliance, comprising a holding means, a hollow body and a receiving area. In particular, the invention relates to such a fastening device for a negative-pressure therapy appliance that can be worn and carried around by the user. The invention further relates to a negative-pressure therapy appliance that comprises a fastening device.

A negative-pressure therapy appliance is a device for providing negative pressure for medical uses, in particular for negative-pressure treatment of wounds on the human or animal body.

Devices for negative-pressure treatment of wounds on the human or animal body and negative-pressure therapy appliances suitable for a negative-pressure treatment of wounds have already been disclosed many times, for example by WO 1996/05873, US 2004/0073151, WO 2011/018132 or WO-2011/018133.

In a conventional device for negative-pressure treatment of wounds on the human or animal body, a negative-pressure therapy appliance communicates with the wound or the wound environment via a suction line, wherein an air-impermeable cover material is provided for leaktight closure of the wound and of the wound environment, such that a negative pressure can be established in the wound space and liquids can be sucked from the wound space into an exudate container. The negative-pressure therapy appliance usually comprises an exudate container. The exudate container is often coupled detachably to the negative-pressure therapy appliance. The exudate container can likewise be accommodated removably in the interior of the negative-pressure therapy appliance or can be present as a separate component. Furthermore, negative-pressure therapy appliances intended mainly for single use are known which comprise an exudate container connected non-releasably to the negative-pressure therapy appliance.

Negative-pressure therapy appliances known from the prior art are either stationary appliances, as described, for example, in WO 1996/05873, or appliances that can be worn on the body of the user and can be carried around for mobile use, as described, for example, in WO 2009/047524. Moreover, negative-pressure therapy appliances are known which are intended for both stationary use and also mobile use, as described, for example, in WO 2011/018132 and in WO 2011/018133. Thus, WO 2011/018132 and WO 2011/018133 each disclose a negative-pressure therapy appliance that can be worn on the body of a user, wherein the negative-pressure therapy appliance is composed of two housing parts. The mechanism generating a negative pressure is arranged in a first housing part of the negative-pressure therapy appliance. A disposable exudate container (canister) that receives body liquids and can be discarded after use forms a second housing part of the negative-pressure therapy appliance. The housing parts can be fixed releasably to each other. Second housing parts of different sizes and with different holding capacities for body liquids can be coupled to the first housing part of the negative-pressure therapy appliance, it being possible to provide smaller canisters, for example with a holding capacity of 300 ml, for mobile use, and larger canisters, for example with a holding capacity of 800 ml, for stationary use. A negative-pressure therapy appliance of this kind is commercially available under the trade name VivanoTec ® (Paul Hartmann AG, Germany).

Negative-pressure therapy appliances for negative-pressure treatment of wounds are used, for example, in hospitals, in general practices or in the home environment of the patient. In hospitals, the negative-pressure therapy appliances are used in operating theaters and ward areas, among other places. Stationary negative-pressure therapy appliances, or mobile negative-pressure therapy appliances in stationary use, normally have to be accommodated in direct proximity to the patient. Portable negative-pressure therapy appliances in mobile use are normally worn on the body of the patient or, for example, carried in a bag. Particularly in stationary use, the problem arises of safely accommodating the negative-pressure therapy appliance and the components connected to the appliance, for example the power supply components or the data communication components, if these are present. The negative-pressure therapy appliance or the power supply and data communication components should not impede the medical personnel treating the patient. Power supply components often comprise a mains cable with a mains plug for connection to the mains, a power supply cable with appliance plug for supplying power to the negative-pressure therapy appliance, and a power pack which is arranged between the two cables and which converts the mains voltage to the voltage required by the negative-pressure therapy appliance. The power packs arranged between power supply cable and mains cable often prove a nuisance in the medical treatment area, as these power packs typically lie unsecured on the floor of the treatment area. A power pack lying loosely on the floor of the treatment area can be a source of danger in hospitals, particularly in operating theaters, and can prove problematic as regards hygiene requirements.

In practice, it is sometimes forgotten to disconnect the negative-pressure therapy appliance from its power supply when it is to be transported. This can cause accidents if a power supply component or data communication component connected to the negative-pressure therapy appliance knocks over other objects present in the treatment area, for example infusion stands.

Negative-pressure therapy appliances are often placed on tables, clamped onto infusion stands, or fixed directly on the hospital bed, for example on vertically or horizontally arranged bars.

Fastening devices for fixing negative-pressure therapy appliances are described in the prior art. For example, WO 2008/036344 discloses a suspension device for fastening a medical appliance, in particular for fastening a negative-pressure therapy appliance. The suspension device of WO 2008/036344 is connected directly to the back of the negative-pressure therapy appliance and comprises a clamping device for releasably fastening the appliance on vertically or horizontally arranged bars. The clamping device is actuated by a rotary knob. To fasten the negative-pressure therapy appliance on or remove it from the bar, the negative-pressure therapy appliance has to be held in one hand, while the other hand presses or releases the rotary knob. The suspension device is not suitable for mounting the negative-pressure therapy appliance on a panel. Secure accommodation of an optionally present power pack is not provided for in connection with the suspension device.

The as yet unpublished German patent application DE102011011831.4 with the title "Device for generating negative pressure for medical applications" describes a holding facility for releasably fastening a negative-pressure therapy appliance on a horizontally or vertically or obliquely arranged strut or bar. The holding facility comprises a rigid holding part, which can be fastened on the housing of the negative-pressure therapy appliance, and a preferably elastic, band-shaped holding means that can be wrapped around a bar and can be turned back onto itself or onto the holding part and closed.

The as yet unpublished German patent application DE102011076868.8 with the title "Device for generating negative pressure for negative-pressure treatment of wounds, with a holding or carrying facility" describes a holding or carrying strap for a portable negative-pressure therapy appliance. According to one embodiment of the invention disclosed in DE102011076868.8, the holding or carrying strap comprises a connection mechanism for connecting the holding or carrying strap to an external support, for example to an infusion stand or to a bed frame.

In the case of the fastening devices described in DE102011011831.4 or in DE102011076868.8, the negative-pressure therapy appliance has to be held by one hand when fastening it or when removing it from a bar, while the other hand closes and opens the fastening mechanism. The devices are likewise unsuitable for mounting the negative-pressure therapy appliance on a panel. Secure accommodation of an optionally present power pack is not provided for in connection with the fastening devices described in DE102011011831.4 or in DE102011076868.8.

It is an object of the present invention to improve a fastening device for releasable fastening of a negative-pressure therapy appliance in such a way that it can be handled and operated in a still more user-friendly way.

In particular, it is an object of the present invention to make available a fastening device that is easy to operate, flexible and safe, intended for an at least optionally portable negative-pressure therapy appliance. The fastening device is intended to allow the negative-pressure therapy appliance to be fastened to suitable objects present in the area where a patient is being treated, for example on a bar, on a strut, on a panel or on a projecting area. It would also be desirable if power supply components or data communication components present on the negative-pressure therapy appliance are safely accommodated and are not left lying around in the treatment area.

According to the invention, this object is achieved by a fastening device for a negative-pressure therapy appliance, comprising a holding means for fixing the fastening device on an object, a hollow body into which one or more power supply components and/or data communication components can be fitted, and a receiving area for receiving the negative-pressure therapy appliance. The object in question is in particular a bar, a strut, a panel or a projecting area.

The hollow body should as far as possible comprise one or more openings for the passage of power cables or communication cables.

The device according to the invention permits safe accommodation and fastening of a negative-pressure therapy appliance on objects that are located in the immediate environment of the patient, for example on a bed frame, on an infusion stand, on a tabletop or on a hoist. The device according to the invention is equally suitable for safely storing the negative-pressure therapy appliance, for example in a storage area of the hospital. The device according to the invention can in this case be advantageously used in the sense of a charging station for at the same time storing the negative-pressure therapy appliance and charging batteries present in portable negative-pressure therapy appliances. Advantageously, power supply components, in particular the power pack and sections of the power supply cable, can be safely and tidily accommodated in the hollow body of the fastening device. Moreover, it has proven advantageous that the power supply components required by the negative-pressure therapy appliance can be fixed safely on the fastening device. This avoids a possible source of danger that can arise if a user, when carrying the negative-pressure therapy appliance away, forgets to first of all disconnect the appliance from the power supply component. As was mentioned at the outset, accidents of this kind can occur when a power supply component or data communication component connected to the negative-pressure therapy appliance knocks over other objects present in the treatment area. An accident of this kind is avoidable when using the fastening device according to the invention, since the power supply components and/or the data communication components can be fixed on the fastening device and as such do not lie loosely about in the treatment area. If a user forgets to remove the power supply component or a data communication component when transporting the negative-pressure therapy appliance, the plug connection between the power supply cable/data cable and the negative-pressure therapy appliance usually comes loose when using the fastening device according to the invention, without damage being caused to the holder or to the negative-pressure therapy appliance.

In the context of the invention, receiving area is understood as that area of the fastening device which receives the negative-pressure therapy appliance, i.e. holds it releasably.

According to an important embodiment of the invention, the holding means comprises areas that permit a form-fit connection, a force-fit connection or a cohesively bonded connection of the device to an object. Accordingly, the fastening device according to the invention can be fixed on an object in particular by clamping, latching, hooking, screwing, nailing, clipping, riveting, welding, fusing, adhesion or by magnetic force of attraction.

Preferably, the fastening device is fixed on an object by clamping, latching or hooking, since this kind of fastening can be done easily and quickly.

For many applications, it proves particularly advantageous if the holding means comprises a clamping mechanism, such that the fastening device can be fixed with a force fit on an object, in particular on a bar, on a panel or on a projecting area. According to this particularly preferred embodiment, the holding means in particular comprises a holding clip, a stirrup clip, a band clip, a snap-on clip or a C-clamp, in particular a screw clamp. Thus, the fastening device can be easily and quickly fastened on an object or removed from the object.

To ensure that the holding means can be clamped in particular with a form fit or force fit onto a bar or a strut, the clamping mechanism preferably comprises an undulated clamping block or jaws with lengthwise depressions. A clamping mechanism of this design can be equally used for clamping the fastening device onto a panel or onto the projecting areas, since the lengthwise depressions present in the undulated clamping block or in the jaws do not impede this.

Jaws optionally present on the clamping means preferably comprise, on all or part of their surface, a rubber covering, such that the force-fit attachment of the clamping means on a bar, on a strut or on a panel is improved, while at the same time damage to the bar or panel is avoided.

According to another important variant of the invention, the fastening device is fixed on an object by screwing, nailing, clipping, riveting, welding, fusing or adhesion. Fixing the fastening device in this way is advantageous if the fastening device is intended to remain permanently at a specific location. For example, it may be desirable for a fastening device according to the invention to be mounted permanently at those areas in the hospital where negative-pressure therapy of wounds is often carried out. For example, these can be ward areas of the hospital that specialize in the treatment of serious, chronic wounds. The fastening device could also be fastened, for example by screwing, to a device which is present in the operating theater and which is intended to hold ready other medical appliances required during the operation. It proves advantageous that the device according to the invention can make ready the power supply components needed for the operation of the negative-pressure therapy appliance, wherein individual power supply components, for example the power pack and/or sections of the power supply cable, are stored safely in the hollow body of the fastening device. Another advantage of a fastening device according to the invention present permanently in the operating theater is that it is then possible to dispense with the sterilization of the device that is otherwise needed when the device is introduced into the operating theater. Instead of fixing it by screwing, it would be equally possible to connect the device to an object in some other way, for example by adhesion or welding. Such non-releasable fixing of the holding means to an object is covered as an embodiment within the scope of the present invention.

According to the invention, the fastening device comprises a hollow body into which one or more power supply components can be fitted, wherein the power supply component is in particular a power pack and/or a cable section and/or an electrical plug connection. Alternatively or in addition, it is possible to introduce one or more data communication components into the hollow space. The data communication components are in particular a data communication cable or plug. However, it is equally possible that active or passive functional components for data communication are introduced into the hollow space, for example a hub, a relay module or a component for linking to a WLAN.

According to one inventive concept that is of particular importance, it is proposed that the fastening device furthermore comprises an insert for receiving one or more power supply or data communication components, which insert can be introduced into the interior of the hollow body. In terms of its shape, the insert should be adapted to the power supply or data communication components that are to be received. If the power supply component comprises, for example, a power pack that is intended to be introduced into the hollow body of the fastening device, then the insert should be able to receive the power pack. The power pack can therefore first be introduced by the user of the fastening device into the insert. Thereafter, the insert is introduced with the power pack into the hollow space of the fastening device. It proves particularly advantageous here if the insert comprises a cable winding, such that unneeded cable sections of power supply or data communication cables can be accommodated.

In the embodiment of the fastening device comprising an insert, the bottom of the receiving area can be formed at least partially by the insert introduced into the hollow space. This may be the case, for example, if the insert can be introduced into the hollow body via an opening arranged in the receiving area. The insert can then be introduced through the receiving area into the hollow body. The insert can be designed such that, after it has been introduced into the hollow body, it closes the hollow body in the manner of a drawer.

Overall, it proves advantageous if the opening for introducing or removing power supply or data communication components or the opening for introducing or removing the insert (if it is present) is arranged in such a way that, after the negative-pressure therapy appliance has been received, the opening is covered by the appliance and is thus closed.

According to another inventive concept of particular importance, it proves advantageous that the receiving area of the fastening device has a shape that complements the negative-pressure therapy appliance, such that the negative-pressure therapy appliance to be received is held substantially captive in the receiving area. For this purpose, the receiving area can, for example, have the shape of a shell in which the lower area of the negative-pressure therapy appliance can be held with a form fit.

In principle, the receiving area and hollow body of the fastening device can be formed as a whole in one piece or, alternatively, can each be formed by one or more separate structural parts.

According to a preferred embodiment of the invention, the receiving area and hollow body as a whole are formed by a single structural part. According to this preferred embodiment, the hollow body and the receiving area are accordingly formed in one piece, and in particular the hollow body and the receiving area are formed in one piece and from the same material. The structural part comprising the hollow body and the receiving area can, for example, be produced from plastic by injection molding in one step. In this case, an upper part of the hollow body can at the same time form at least a partial area of the bottom of the receiving area.

According to another particularly preferred embodiment of the invention, the hollow body and the receiving area are formed from two or more separate structural parts, and the structural parts for producing the fastening device are then connected to one another preferably by screwing, adhesion or welding. The structural parts can in this case each be made of the same material, or they can each be produced from one or more different materials.

According to another inventive concept, it is proposed that the fastening device comprises a coupling element which is connected releasably or non-releasably to the negative-pressure therapy appliance. In this embodiment, the receiving area is designed in such a way that at least the coupling element can be received in the receiving area. It is also possible that the coupling element and a part of the negative-pressure therapy appliance connected to the coupling element can be received in the receiving area.

A coupling element for use with a fastening device as described in the present disclosure is therefore likewise the subject of the present invention.

In particular, it is advantageous if the receiving area has a shape complementing the coupling element, or a shape complementing the coupling element and a negative-pressure therapy appliance connected to the latter.

The coupling element can, for example, be a plate-shaped element that can be connected releasably to the bottom of the negative-pressure therapy appliance. The outer shape (contour) of the coupling element can correspond substantially to the outer shape (contour) of the bottom of the negative-pressure therapy appliance. For the releasable connection of the coupling element to the negative-pressure therapy appliance, a receiver for the coupling element is preferably provided on the negative-pressure therapy appliance. The receiver can, for example, be a thread present in the bottom of the negative-pressure therapy appliance, such that the coupling element can be secured on the negative-pressure therapy appliance via a screw present on the coupling element. The coupling element can remain permanently connected to the negative-pressure therapy appliance. If appropriate, elements present on the bottom of the negative-pressure therapy appliance, for example rubber soles, can also be present on the underside of the coupling element, such that the negative-pressure therapy appliance, if not located in the fastening device, can be placed, with the coupling element secured to it, on a flat surface.

According to an advantageous embodiment of the invention, the receiving area is substantially plate-shaped, the plane of the plate being arranged horizontally during the use of the device.

According to another particularly preferred embodiment, the fastening device comprises a coupling element that is connected non-releasably to the negative-pressure therapy appliance. According to a refinement of this particular inventive concept, the coupling element represents a housing part of the negative-pressure therapy appliance. Therefore, in this embodiment, the negative-pressure therapy appliance is adapted in terms of its outer shape to the receiving area of the fastening device.

According to an independent inventive concept, it proves advantageous if the receiving area comprises a closure means, such that the negative-pressure therapy appliance can be locked releasably.

The closure means can, for example, be a strap, a locking lever, a locking pin, or a hook-in mechanism. A magnetic closure would also be conceivable. The closure means ensures a secure connection of the fastening device to the negative-pressure therapy appliance, such that the negative-pressure therapy appliance cannot fall.

According to a simple embodiment, the closure means can be a strap which is present on the fastening device and which, in order to secure the negative-pressure therapy appliance, is placed around the housing of the appliance.

The closure means is preferably a latching closure means, which can lock the negative-pressure therapy appliance releasably.

The closure means can engage in this case on the housing of the negative-pressure therapy appliance or, if there is one, on the coupling element.

According to a particularly preferred embodiment, the coupling element and/or the negative-pressure therapy appliance has one or more recesses in which the closure means present on the receiving area can engage. In particular, the coupling element has a recess in which the closure means present on the receving area can engage.

In a further embodiment of the invention, the closure means can be moved in the direction of release by a manually operated actuating member. Preferably, the manually operated actuating member is provided on the edge of the receiving area and on the side of the fastening device lying opposite the holding means. The actuating member is designed in particular as a press-in button or as a removable and, for example, ring-shaped grip in which a single finger can engage.

Ideally, it should be possible for the negative-pressure therapy appliance to be secured in the fastening device or removed from the fastening device using only one hand. According to a particularly preferred embodiment, the negative-pressure therapy appliance can therefore be fixed on the fastening device and/or released from the fastening device using one hand.

According to another advantageous development, one or more abutment elements are present in the receiving area, such that the coupling element is oriented with a form fit when brought into contact with the receiving area. Preferably, the one or more abutment elements comprise one or more recesses in which one or more springs or protruding portions present on the coupling element can engage, such that the coupling element is oriented with a form fit when brought into contact with the receiving area.

With a view to user-friendly attachment of negative-pressure therapy appliance and fastening device, it proves advantageous if the negative-pressure therapy appliance is moved from above, at a slight inclination to the vertical, toward one or more abutment elements and can then be pressed downward until a latching closure means, if present, comes into latching engagement, wherein the negative-pressure therapy appliance is brought to the vertical position. The latching engagement of the closure means is normally accompanied by a clearly audible click, so the user receives an acoustic signal when the negative-pressure therapy appliance is locked in the fastening device.

In order to facilitate the insertion and orientation of the negative-pressure therapy appliance in the fastening device, the edge of the receiving area, in another preferred embodiment, has a web or bead which extends partially or completely around the receiving area, such that the coupling element is oriented with a form fit when brought into contact with the receiving area.

According to another particularly preferred embodiment, several abutment elements and a web or bead extending partially or completely around the receiving area can be present at the same time in the receiving area. In order to improve the withdrawal of the negative-pressure therapy appliance from the fastening device using just one hand, it would be conceivable in this context to also design the receiving area in such a way that the negative-pressure therapy appliance is pressed out of the receiving area as soon as and for as long as the latching closure means is released. This can be achieved, for example, if an element providing a restoring force, for example a spring, is present in the receiving area. Thus, after the latching closure means has been released, the negative-pressure therapy appliance is pressed slightly out of the receiving area but, on account of the abutment elements present in the receiving area and/or of the edge extending around the receiving area, remains on the fastening device and cannot fall. When the negative-pressure therapy appliance is introduced into the fastening device, the appliance, in this particularly preferred embodiment, has to be pressed into the receiving area counter to the resistance of the element providing a restoring force, until the closure means comes into latching engagement. The latching of the closure means is normally accompanied by a clearly audible click.

According to the above-described embodiment, which is particularly advantageous in practice, the receiving area comprises one or more abutment elements and/or an edge extending around the receiving area, a latching closure means, and an element that provides a restoring force and presses the negative-pressure therapy appliance out of the receiving area, such that the negative-pressure therapy appliance, when it is brought into contact with the receiving area, has to be pressed counter to a restoring force until the closure means comes into latching engagement.

So as to be able to fix the fastening device on any kind of bars, struts, panels or protruding areas present in hospitals, it proves very advantageous if the receiving area can be rotated relative to the holding means. According to the embodiment proposed here, the fastening device comprises a pivot joint, such that the receiving area can be rotated relative to the holding means. The pivot joint is preferably designed such that it can lock. According to a particularly preferred embodiment, the pivot joint can lock releasably at the 0°, 45°, 90°, 135°, 180°, 225°, 270° or 315° position, such that the device can be mounted on a vertical, on a horizontal or on an obliquely arranged bar or panel.

The means (rotary lock) acting on the pivot joint, and causing the pivot joint to lock, preferably comprises a lever, a bow or a push-button. In particular, the lever, the bow or the push-button is designed in such a way that it can be released with one hand.

According to another particularly preferred embodiment, the pivot joint can lock releasably at the 0°, 90°, 180° or 270° position, such that the device can be mounted on a vertical or on a horizontal bar, strut or panel, in particular on a tabletop, on a vertical bed post, on a horizontal element of a bed frame or on an infusion stand.

Therefore, along with the receiving area, the hollow body connected firmly to the receiving area is also rotatable relative to the holding means. The pivot joint can be covered by a cladding, in particular by a cladding that encloses the pivot joint like a housing.

According to a refinement of the inventive concept, it would be possible to integrate into the receiving area a plug for the power supply, in such a way that the negative-pressure therapy appliance, when introduced into the fastening device, is connected to the power supply. For this purpose, a suitable mating piece is needed on the negative-pressure therapy appliance. Alternatively or in addition, it would be equally possible for a data exchange interface, in particular a USB interface, to be integrated in the receiving area of the fastening device in such a way that the negative-pressure therapy appliance, when introduced into the fastening device, is connected to the data communication line. According to the special embodiment of the invention described here, the fastening device thus serves not only for fixing the negative-pressure therapy appliance, but also for linking the negative-pressure therapy appliance to a power supply and/or to a data communication line in the sense of a docking station.

The fastening device according to the invention can be made from suitable materials that are customarily used for the described purpose. The components are normally made from plastic and/or metal. Plastics are particularly suitable for producing the receiving area and the hollow body. The holding means and the pivot joint, if present, can be made at least partially from a metal.

In practical application, the user can first of all secure the fastening device on a suitable object present in the area of the patient, for example by clamping it to a bed strut. The user can then introduce power supply components or data communication components into the hollow body of the fastening device, in which case the mains cable, the appliance power supply cable and/or optional data communication cables are guided out of the hollow body through openings in the hollow body. In particular, the user can secure the power pack in the insert (if present) and can place surplus cable sections around the cable winding (if present) of the insert. The insert is then introduced into the hollow body. The negative-pressure therapy appliance is brought into contact with the receiving area of the fastening device and optionally secured, for example by a latching closure means (if present). The appliance power supply cable guided out of the interior of the hollow body is connected to the negative-pressure therapy appliance. The negative-pressure therapy appliance is now ready for use and is safely accommodated in immediate proximity to the patient.

The present invention further relates to an apparatus for negative-pressure therapy of wounds, comprising a negative-pressure therapy appliance and a fastening device as described in the present application.

The present invention relates in particular to an apparatus for negative-pressure therapy of wounds, comprising a negative-pressure therapy appliance that can be worn on the body of a user and a fastening device as described in the present application.

The present invention further relates to an apparatus for negative-pressure therapy of wounds, comprising a negative-pressure therapy appliance that can be worn on the body of a user and a fastening device as described in the present application, wherein the negative-pressure therapy appliance comprises a disposable exudate container, which can be discarded after use and serves to receive body liquids, in particular wound secretions aspirated from a wound, and also comprises an attachment piece for a suction line that leads for this purpose to the body. Preferably, the mechanism generating the negative pressure is arranged in or on a first housing part of the negative-pressure therapy appliance, while the exudate container forms the second housing part of the negative-pressure therapy appliance or is arranged in or on the second housing part. The housing parts can be fixed releasably to each other. Preferably, the negative-pressure therapy appliance has fastening means such that it can be worn on the body of the user and can be carried around.

According to a particularly preferred embodiment, when the negative-pressure therapy appliance is carried around on the body of the user (mobile use), the first housing part is directed away from the body and the second housing part is directed toward the body, wherein both housing parts have a substantially disk-shaped design and bear on each other via a substantially vertically disposed dividing plane.

According to another particularly preferred embodiment, the housing parts of the negative-pressure therapy appliance can be fixed releasably to each other by a locking or engaging means that has a snap-fit action, a latching action or some other form-fit action. Moreover, according to this particularly preferred embodiment, the locking or engaging means can be brought to the release position by a manually operated actuating member and the first and/or second housing part is designed for manual engagement. The negative-pressure therapy appliance or the first or the second housing part can be gripped, and one housing part can be detached from the other housing part. Since the manually operated actuating member for the locking or engaging means is provided in the area of the manual grip, a user can release the locking or engaging means with just one hand and thus at one and the same time grip one housing part and release and detach it from the other housing part.

According to a particularly preferred embodiment, the present invention relates to an apparatus for negative-pressure therapy of wounds comprising a negative-pressure therapy appliance as described in patent application WO2011/018132 or WO2011/018133 and also a fastening device as described in the present application. Reference is hereby expressly made to the content of patent application WO2011/018132 or WO2011/018133.

The present invention further includes a method for fastening a negative-pressure therapy appliance, which method comprises providing a fastening device
providing a negative-pressure therapy appliance
optional: providing an insert
fixing the fastening device on an object, for example on a panel or on a bar
optional: rotating the receiving area relative to the holding means, such that the receiving area is oriented horizontally optional: introducing the power pack into the insert and, if appropriate, placing unneeded cable sections around the cable winding of the insert introducing power supply components and/or data communication components into the hollow body, wherein the mains cable, the appliance power supply cable and/or the optional data communication cable are guided out of the interior of the hollow body through openings in the hollow body bringing the negative-pressure therapy appliance into contact with the receiving area of the fastening device optional: securing the negative-pressure therapy appliance in the receiving area, preferably by a latching closure means connecting the appliance power supply cable to the negative-pressure therapy appliance A negative-pressure therapy apparatus ready for use in the treatment of wounds in patients comprises at least a negative-pressure therapy appliance, a negative-pressure wound dressing, a negative-pressure attachment piece (port), and a drainage hose connecting the wound dressing to the negative-pressure therapy appliance.

BRIEF DESCRIPTION OF THE DRAWINGS

Further features, details and advantages of the invention will become clear from the appended patent claims and from the drawings, and also from the following description of preferred embodiments of the device according to the invention. For the features of the patent claims, protection is claimed separately and in any combination, irrespective of the dependency of the claims. In the drawings:

FIGS. 1 A and B show different views of a first preferred embodiment of the fastening device according to the invention, with a negative-pressure therapy appliance fastened thereon.

FIGS. 2 A to C show different views of another preferred embodiment of the fastening device according to the invention, with a negative-pressure therapy appliance fastened thereon.

FIG. 3 A shows an insert provided for introduction into the interior of the hollow body.

FIG. 3 B shows a fastening device according to the invention as shown in FIG. 2, with the insert not located in the hollow body. The holding means present on the fastening device has been omitted from the figure.

FIG. 3 C shows a fastening device according to the invention as shown in FIG. 2, with the insert located in the hollow body. The holding means present on the fastening device has been omitted from the figure.

FIG. 4 A shows a plan view of a fastening device according to the invention as shown in FIG. 2, with the insert located in the hollow body. The holding means present on the fastening device has been omitted from the figure.

FIGS. 4 B and C show different views of the coupling element.

FIG. 4 D shows a plan view of a fastening device according to the invention as shown in FIG. 2, with the coupling element present in the receiving area. The holding means present on the fastening device has been omitted from the figure.

FIG. 4 E shows a negative-pressure therapy appliance with a coupling element fastened to the appliance.

DETAILED DESCRIPTION OF PREFERRED EMBODIMENT(S)

Figure 1:
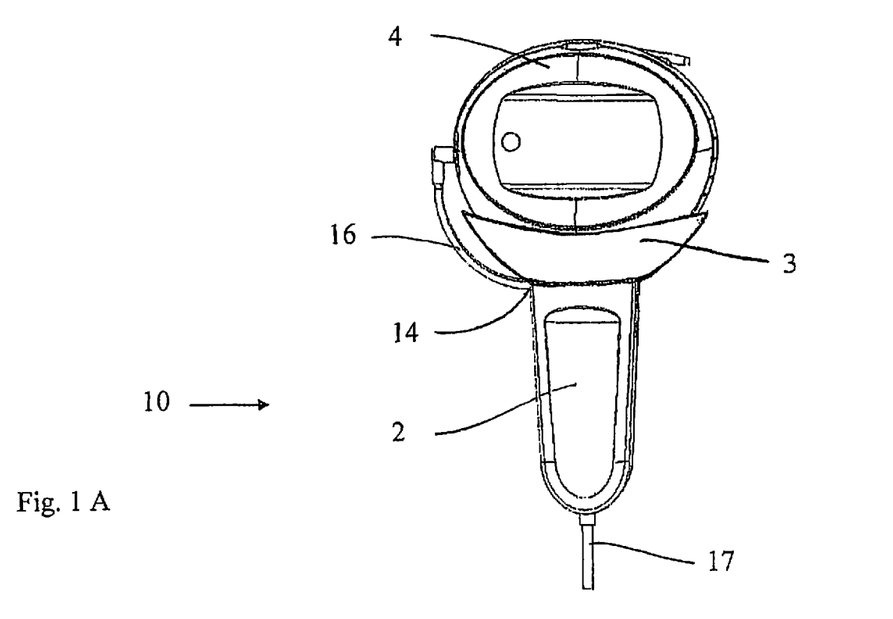
Figure 3:
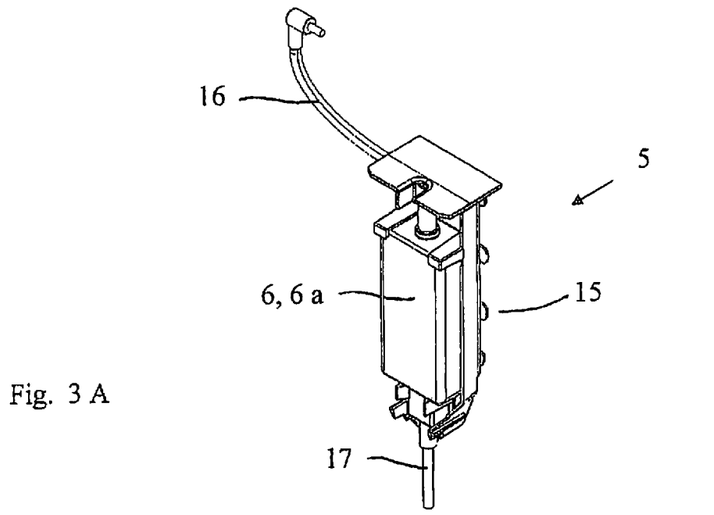

FIG. 1 A shows a first preferred embodiment of the fastening device 10 according to the invention from the front, with a negative-pressure therapy appliance 4 fastened thereon. The negative-pressure therapy appliance 4 lies substantially captive in a dish-like receiving area 3, wherein the receiving area 3 has a shape complementing the lower part of the negative-pressure therapy appliance 4. Toward the bottom, the receiving area 3 is adjoined by the hollow body 2. Power supply components 6, for example a power pack 6 a (not visible in FIG. 1 A; see FIG. 3 A), and unneeded sections of cable, are introduced into the hollow body. The mains cable 17 is guided out of the hollow body 2 through an opening at the lower end of the hollow body 2. The appliance power supply cable 16, which connects the power pack 6 a to the negative-pressure therapy appliance 4, is guided out of the hollow body 2 through the opening 14. The holding means for fixing the fastening device on an object is not visible in FIG. 1 A, since the holding means is completely concealed by the hollow body 2 and the receiving area 3. The first preferred embodiment of the fastening device, shown from the front in FIG. 1 A, is shown in a side view in FIG. 1 B, such that the holding means 1 can be seen. In the embodiment shown in FIGS. 1 A and B, the holding means 1 is designed as a clamping means. The fastening device 10 can be mounted releasably on bars, struts, panels or projecting areas with the aid of the holding means 1 designed in the form of a screw clamp. The receiving area 3 and the hollow body 2 connected to the receiving area are rotatable with respect to the holding means 1, since a pivot joint is arranged between the hollow body 2 and the holding means 1. The pivot joint is covered by a cladding 24 and is consequently not visible in FIG. 1 B. The cladding 24 encloses the pivot joint like a housing. The pivot joint can lock releasably, by means of a rotary lock, preferably at the 0°, 45°, 90°, 135°, 180°, 225°, 270° or 315° position. The rotary lock can be freed with a control element. In the illustrative embodiment shown in FIG. 1 B, the control element is the downwardly extending lever 26, which can be released with one hand. Thus, the fastening device 10 can be secured on any kind of vertically, horizontally or obliquely arranged bar or panel.

Figure 2:
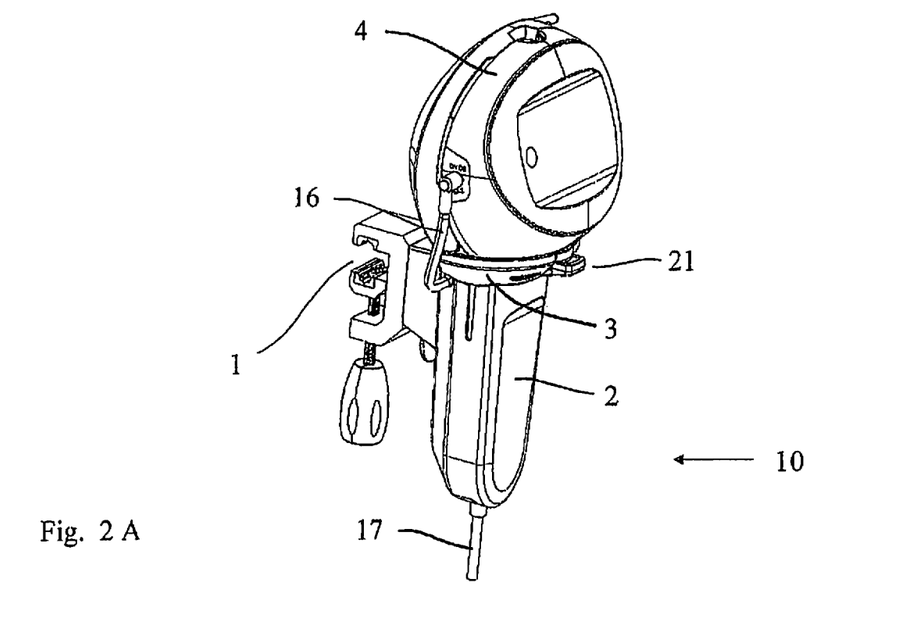

FIGS. 2 A to C show another preferred embodiment of the fastening device 10 according to the invention, with a negative-pressure therapy appliance 4 fastened thereon, obliquely from the front (FIG. 2 A), from the side (FIG. 2 B) and from in front (FIG. 2 C). In the illustrative embodiment shown in FIGS. 2 A-C, the receiving area 3 is shallower compared to the illustrative embodiment shown in FIGS. 1 A and B. In the preferred embodiment according to FIGS. 2 A to C, the receiving area 3 is provided for receiving a coupling element (not visible in FIGS. 2 A to C; see FIGS. 4 B to E, reference sign 8). Moreover, the receiving area 3 comprises a latching closure means with a grip 21, such that the negative-pressure therapy appliance 4 and the coupling element connected to the negative-pressure therapy appliance 4 can be locked releasably in the receiving area 3 of the fastening device 10. As in the example shown in FIGS. 1 A and B, power supply components can be accommodated in the interior of the hollow body 2. For this purpose, an insert (not visible in FIGS. 2 A to C) for receiving power supply components is located in the interior of the hollow body 2. FIGS. 2 A to C also reveal the mains cable 17 guided out of the hollow body 2 through an opening present at the lower end of the hollow body 2, and also the appliance power supply cable 16 guided out through a further opening 14 in the hollow body 2. The holding means 1 concealed in FIG. 2 C by the hollow body 2 and the receiving area 3 can be seen in FIGS. 2 A and 2 B. As in FIGS. 1 A and B, the holding means 1 is designed in the form of a screw clamp, such that the fastening device 10 could be screwed, for example, onto a bar or bed strut. The holding means 1 comprises jaws, in which oblong depressions are present. Depressions of this kind make it easier to mount the holding means 1 on bar-like objects.

As in the illustrative embodiment shown in FIGS. 1 A and B, a releasably lockable pivot joint is present between the holding means 1 and the hollow body 2, the pivot joint again being covered by a cladding 24.

The pivot joint can lock releasably, by means of a rotary lock, preferably in the 0°, 45°, 90°, 135°, 180°, 225°, 270° or 315° position. The rotary lock is freed by means of the lever 26.

The opening 14 can be seen only in the side view in FIG. 2 B. A further opening can be present on the opposite side.

FIG. 3 A shows the insert 5 provided for introduction into the interior of the hollow body 2. The insert 5 is provided to receive one or more power supply components 6 (for example a power pack 6 *a*, a cable or an electrical plug connection) and/or data communication components (for example a data communication cable, a component for linking to a WLAN, or a plug). In the embodiment shown in FIG. 3 A, the power supply components 6 to be fitted into the interior of the hollow body 2 by means of the insert 5 comprise a power pack 6 *a*, which is secured on the insert 5, and cable sections of the mains cable 17, and cable sections of the appliance power supply cable 16. Holding elements present on the insert 5 serve to secure the power pack 6 a. In the embodiment shown here, the insert 5 is made of plastic.

The insert 5 is designed in such a way that it can be pushed with a form fit into the interior of the hollow body 2. In the embodiment shown here, the insert 5 is guided into the interior of the hollow body 2 through the opening 27 (see FIG. 3 B). Before the insert 5 is introduced into the hollow body, the mains cable 17 has to be guided through the hollow body via an opening that is present at the lower end of the hollow body 2. Likewise, the appliance power supply cable 16 has to be guided through the opening 14 (see FIG. 2 B).

A cable winding 15 present on the rear face of the insert 5 can be seen in FIG. 3 A. The cable winding 15 serves to accommodate cable sections that are not needed (for example sections of the appliance power supply cable).

In FIG. 3 B, the embodiment of the fastening device 10 shown in FIGS. 2 A to C is shown without the insert 5 located therein. The opening 27 for receiving the insert 5 can be seen. FIG. 3 C shows the fastening device 10 after the insert 5 has been introduced into the interior of the hollow body 2. The opening 27 is completely closed by a plate located on the upper portion of the insert 5. The fastening device 10 also comprises a holding means. However, for the sake of clarity, the holding means 1 (see FIGS. 2 A and B) has not been depicted in FIGS. 3 B and 3 C.

Figure 4:
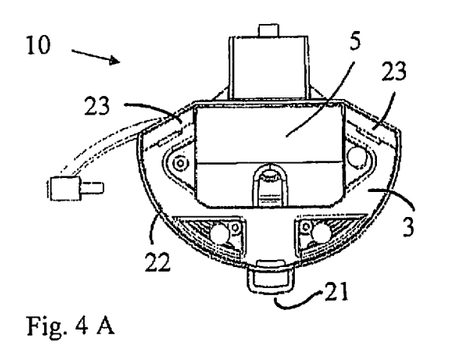

In FIG. 4 A, the embodiment of the fastening device 10 shown in FIGS. 2 A to C is shown from above, the negative-pressure therapy appliance 4 having been omitted from the depiction. For the sake of clarity, the similarly present holding means 1 (see FIGS. 2 A and 2 B) has not been shown here. In the fastening device 10 shown in FIG. 4 A, the insert 5 has been introduced into the interior of the hollow body 2, such that the opening 27 (see FIG. 3 B) is completely closed by the upper part of the insert 5. A web 22 extending around the receiving area 3 can be seen, and also the laterally arranged abutment elements 23. The web 22 and the abutment elements 23 facilitate the mounting and the form-fit orientation of the negative-pressure therapy appliance 4 that is to be mounted on the fastening device 10. The latching closure means comprises a ring-shaped grip 21, such that the closure means can be freed by pulling on the ring-shaped grip 21 in order to remove the negative-pressure therapy appliance 4.

The coupling element 8 is shown in FIGS. 4 B and 4 C. The coupling element 8 comprises a screw (not shown in FIGS. 4 B and 4 C) which is provided for mounting the coupling element 8 on the bottom of the negative-pressure therapy appliance 4. For this purpose, the screw is guided through the bore 28 and screwed tightly on the negative-pressure therapy appliance. Moreover, according to a particularly advantageous embodiment, the coupling element 8 comprises one or more projections or spring elements 29. When the negative-pressure therapy appliance provided with a coupling element 8 is fitted in place, these projections or spring elements each engage in an opening or groove present in the receiving area, preferably at the edge. According to a particularly preferred embodiment of the fastening device 10, a groove (not visible in FIGS. 2 to 4) for receiving the springs 29 present on the coupling element is provided on each of the two abutment elements 23.

FIG. 4 D shows the fastening device 10 in order to illustrate the fit between coupling element 8 and receiving area 3, with the coupling element 8 inserted from above (normally, however, the coupling element 8 is located on the negative-pressure therapy appliance 4). It will be seen that the coupling element 8 is held with a form fit in the receiving area 3 by means of the abutment elements 23 and the peripheral edge 22.

When the negative-pressure therapy appliance 4 connected to the coupling element 8 is introduced into the fastening device 10, the closure means engages with a latching action in the coupling element 8. By pulling on the grip 21 belonging to the closure means (the ring-shaped grip 21 has been exposed for clarity in FIG. 4 D), the closure means is freed or unlocked and releases the negative-pressure therapy appliance 4, such that the latter can be removed.

FIG. 4 E shows a negative-pressure therapy appliance 4 with a coupling element 8 secured on the appliance. In the particularly advantageous embodiment of the invention shown here, the coupling element 8 is screwed onto the negative-pressure therapy appliance 4. For this purpose, a thread is located on the underside of the negative-pressure therapy appliance 4.

During normal operation of the negative-pressure therapy appliance, the coupling element 8 can remain connected at all times to the negative-pressure therapy appliance. By virtue of the flat underside of the coupling element 8, the negative-pressure therapy appliance 4, with a coupling element 8 secured thereon, can be set down at any time for example on a flat surface or can be worn on the body of a user. The negative-pressure therapy appliance 4 is in particular a negative-pressure therapy appliance that can be worn on the body of a user, for example the negative-pressure therapy unit VivanoTec® manufactured by Paul Hartmann AG.

What is claimed is:

1. A fastening device (10) for a negative-pressure therapy appliance (4), comprising:
    a holding means (1) for fixing the fastening device on an object,
    a hollow body (2) into which one or more power supply components (6) and/or data communication components can be fitted,
    a receiving area (3) for receiving the negative-pressure therapy appliance (4) such that the negative-pressure therapy appliance is releasably locked therein
    wherein the hollow body (2) is adjoined to the receiving area (3) and a coupling element (8) which is releasably connectable or non-releasably connected to the negative-pressure therapy appliance (4), wherein the receiving area (3) can receive the coupling element (8).

2. The fastening device (10) according to claim 1, wherein the holding means (1) comprises areas that permit a form-fit connection, a force-fit connection or a cohesively bonded connection of the fastening device to an object by clamping, latching, hooking, screwing, nailing, clipping, riveting, welding, fusing, adhesion or by magnetic force of attraction.

3. The fastening device (10) according to claim 1, wherein the holding means (1) comprises a clamping mechanism, such that the fastening device (10) can be fixed with a force fit on the object.

4. The fastening device (10) according to claim 1, wherein the holding means (1) comprises a holding clip, a stirrup clip, a band clip, a snap-on clip or a C-clamp or a screw clamp.

5. The fastening device (10) according to claim 1, wherein the power supply component (6) is a power pack (6a) and/or a section of a cable and/or an electrical plug connection.

6. The fastening device (10) according to claim 1, wherein the hollow body (2) comprises one or more openings (14) for the passage of cable sections.

7. The fastening device (10) according to claim 1, further comprising an insert (5) for receiving one or more power supply components (6) and/or data communication components, wherein the insert (5) is introduced into an interior of the hollow body (2).

8. The fastening device (10) according to claim 7, wherein the insert (5) comprises a cable winding (15).

9. The fastening device (10) according to claim 1, wherein the receiving area (3) has a shape complementing the negative-pressure therapy appliance (4), such that the negative-pressure therapy appliance (4) is held substantially captive in the receiving area (3).

10. The fastening device (10) according to claim 1, wherein the coupling element (8) can be secured releasably on the negative-pressure therapy appliance (4).

11. The fastening device (10) according to claim 1, wherein the coupling element (8) is secured non-releasably on the negative-pressure therapy appliance (4), or wherein the coupling element (8) is a housing part of the negative-pressure therapy appliance (4).

12. The fastening device (10) according to claim 1, wherein the receiving area (3) comprises a closure means, such that the negative-pressure therapy appliance (4) is locked releasably on the fastening device (10), wherein the closure means is a latching closure means, which comprises a grip (21).

13. The fastening device (10) according to claim 12, wherein the coupling element (8) and/or the negative-pressure therapy appliance (4) have one or more recesses into which the closure means present on the receiving area (3) can engage.

14. The fastening device (10) according to claim 1, wherein the receiving area (3) has one or more abutment elements (23), such that the coupling element (8) and/or the negative-pressure therapy appliance (4) are oriented with a form fit when brought into contact with the receiving area (3).

15. The fastening device (10) according to claim 1, wherein the edge of the receiving area (3) has a web or bead (22) extending partially or completely around the receiving area (3), such that the coupling element (8) and/or the negative-pressure therapy appliance (4) are oriented with a form fit when brought into contact with the receiving area (3).

16. The fastening device (10) according to claim 1, wherein the negative-pressure therapy appliance (4) can be fixed on and/or removed from the fastening device (10) with one hand.

17. A coupling element (8) for use with a fastening device (10) according to claim 1.

18. An apparatus for negative-pressure therapy of wounds, comprising a negative-pressure therapy appliance (4) that can be worn on the body of a user, and a fastening device (10) according to claim 1.

* * * * *